United States Patent [19]

Tóth et al.

[11] Patent Number: 4,493,727
[45] Date of Patent: Jan. 15, 1985

[54] PLANT GROWTH REGULATING METHOD

[75] Inventors: István Tóth, Sajóbábony; József Nagy, Miskolc; Zsolt Dombay, Miskolc; Erzsebet Grega née Tóth, Miskolc; Ibolya Horváth, Szeged; László Vigh, Szeged; Tibor Farkas, Szeged, all of Hungary

[73] Assignee: Északmagyarországi Vegyimüvek, Sajóbábony, Hungary

[21] Appl. No.: 438,746

[22] Filed: Nov. 3, 1982

[51] Int. Cl.³ .................. A01N 37/18; A01N 43/46
[52] U.S. Cl. ................................ 71/088; 71/118
[58] Field of Search ............... 71/118, DIG. 1, 88

[56] References Cited

U.S. PATENT DOCUMENTS

| | | | |
|---|---|---|---|
| 3,133,808 | 5/1964 | Hamm | 71/118 |
| 3,429,690 | 2/1969 | Olin | 71/118 |
| 3,475,155 | 10/1969 | Ishida et al. | 71/118 |
| 3,829,306 | 8/1974 | Ratts | 71/118 |
| 4,021,224 | 5/1977 | Pallos et al. | 71/118 |
| 4,033,756 | 7/1977 | Hoffmann | 71/118 |
| 4,053,297 | 10/1977 | Richter | 71/118 |
| 4,150,969 | 4/1979 | Dudkowski | 71/DIG. 1 |

FOREIGN PATENT DOCUMENTS 2510940 9/1976 Fed. Rep. of Germany ........ 71/118

OTHER PUBLICATIONS

Fawcett et al., "Germination Stimulation, etc;" (1975), CA83, No. 142908q., (1975).
Heywood, "N-Dichloroacetyl derivatives, etc;"(1954), CA50, No. 1083c., (1956).
Hamm et al. I, "Relation of Herbicidal, etc;", (1956), J. Agr. & Food Chem. 4, pp. 518-522, (1956).
Hamm et al. II, "Effect of Variations, etc;" (1957), J. Agr. & Food Chem. 5, pp. 30-32, (1957).
Stephenson et al., "Structure-Activity, etc;" (1979), J. Agr. Food Chem., vol. 27, No. 3, pp. 543-547, (1979).
Black et al., "Promotion of Germination, etc;" , (1965), CA64, p. 5681g., (1966).
Chatterjee et al., "Regulation of Plant, etc;" ,(1973), CA82, No. 27083j, (1975).
J. Agric. Food Chem., vol. 26, No. 1, pp. 137-140, 1978.
Houben-Weil: Methoden der Organischen Chemie Bd. XI/2, pp. 3-37, 1958.

Primary Examiner—Richard L. Raymond
Attorney, Agent, or Firm—Karl F. Ross; Herbert Dubno

[57] ABSTRACT

The invention relates to a plant growth regulating composition which contains as active agent a compound of general formula (I)

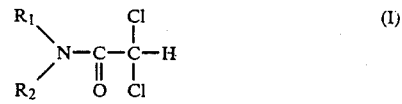

wherein
R₁ and R₂ can be identical or different and can stand for hydrogen, a $C_{1-4}$ straight or branched alkyl group, cyclohexyl, phenyl, chlorophenyl, alkylphenyl, benzyl or alkylbenzyl group, or R₁ and R₂ can together with the N atoms form a heterocyclic ring.

The growing of plants can be stimulated and the green weight can be increased to a significant degree by the treatment carried out with the composition of the invention.

11 Claims, No Drawings

PLANT GROWTH REGULATING METHOD

The invention relates to a plant growth regulating composition which contains 5 to 80 percent by weight of at least one of the compounds of formula (I)

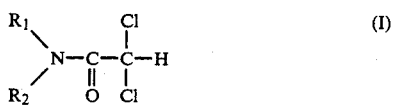

10 to 95 percent by weight of a solid and/or liquid carrier as well as 0.5 to 15 percent by weight of a surface-active agent.

In formula (I) $R_1$ and $R_2$ can be identical or different and can stand for hydrogen, a $C_{1-4}$ straight or branched alkyl group, cyclohexyl, phenyl, chlorophenyl, alkylphenyl, benzyl or alkylbenzyl group, or $R_1$ and $R_2$ can together with the N atom form a heterocyclic ring.

A wide range of compounds is known from the literature which are capable of regulating the growth of plants. One group of these compounds—called regulators—is constituted by natural or synthetic hormones (Kölcsei M., Nádasy M,: Magyar Kémikusok Lapja 34 (3), 122–126 1979). Such compounds are the natural or synthetic auxins, the gibberellins, the cytoquinines and the abscisins or the synthesized analogs thereof.

The chloro choline chloride which inhibits the growth of the cells lengthwise has been known for a long time and is used widely for strengthening corn stalks.

It is known from U.S. patent specification No. 3,156,544 that some (2-halogenoethyl)trialkylammonium salts, especially the (2-chloroethyl)trimethylammonium chloride, possess a plant growth and yield regulating activity. Germination inhibiting activity and longitudinal cell growth inhibiting activity of some pyrimidine derivatives, such as 2-methylthio-4-ethylamino-5-nitro-6-methyl-aminopyrimidine and their salts are disclosed in Hungarian patent specification No. 164,885.

According to Hungarian patent specification No. 170,761 some phthalimide derivatives increase the speed of sprouting and growing.

Our experiments concerning plant growth regulation show that the growing of plants can be stimulated and the green weight can be increased to a significant degree by the treatment carried out with the composition of the invention.

The composition of the invention contains 10 to 95 percent by weight of at least one solid and/or liquid carriers, 0.5 to 15 percent by weight of at least one surface-active agents and 5 to 80 percent by weight of compounds of formula (I).

The substituted halogeno-carboxylic acid amides of formula (I) are known from the literature but their plant growth stimulating activity is not known.

The disubstituted acid amides can be prepared by known methods (e.g. Houben-Weill: Methoden der Organischen Chemie, B: XI[2]; pp. 3–37; 1958. The most widely used method is the reaction of a halogeno-carboxylic acid chloride with a secondary amine. The compounds of formula (I) can be prepared, however, by the reaction of a halogeno-carboxylic acid with a secondary amine in the presence of phosphorus trichloride or phosphoroxy chloride or with simultaneous introduction of phosgene (when carbamoyl chloride forms as intermediate product).

The variety of the preparing processes renders possible to provide the compounds of formula (I) in an easy and economical way.

The preparation of the compositions of the invention is illustrated with the aid of the following, examples.

EXAMPLE 1

52 parts by weight of N-(dichloroacetyl)hexamethylenimide and 2 parts by weight of phenol are placed into an apparatus provided with a mixer and then 17 parts by weight of xylene and 19 parts by weight of methylene chloride are added. The reaction mixture is stirred until the solid substances dissolve, then 10 parts by weight of a mixture of dodecyl-benzene-sulfonic acid-calcium (Atlox 4857B) and polyoxy-ethylene-alkyl-phenol (Atlox 3400B) are added. After the dissolution of the surface-active agents the solution is filtered off and an emulsion concentrate is obtained which has a concentration of 50 percent by weight and can be used by spraying with water.

EXAMPLE 2

In 7.5 parts by weight of water and 2.5 parts by weight of polyglycol ether (Polyglycol 1000) are dissolved, then 59 parts by weight of technical vaseline oil, 1 part by weight of amorphous silicic acid (Ultrasyl VN 3), 10 parts by weight of fatty alcohol polyglycol ether (Emulsogen M) and 20 parts by weight of N-(dichloroacetyl)hexamethylenimide are added. The mixture is ground in a laboratory pearl mill by the addition of 200 g. of pearls (diameter 1.5 mm) with a speed of 775 r.p.m. for 1.5 hours. Then the pearl charge is separated on a sieve from the produced FW of 20 percent by weight. The product is stable for 2 hours, after 24 hours some sediment reversibly separates out (it can be dispersed by shaking).

EXAMPLE 3

52 parts by weight of technical N-(dichloroacetyl)-hexamethylenimide, 38 parts by weight of amorphous silicic acid (Ultrasyl VN 3), 3.5 parts by weight of preliminary condensate of cresol-formaldehyde (Dispergiermittel Hoe 1494), 1.5 parts by weight of aliphatic sulfonic acid sodiumsalt (Netzer IS) and 5 parts by weight of powdered sulfite waste-liquor are mixed and ground in a mill of type Alpine 100 LU.

The thus-obtained WP containing 50 percent by weight of an active agent has a
floatability (in 1 percent by weight in water): 91.98%, wet sieve residue (on a 45μ sieve): 9.69%.

EXAMPLE 4

5 parts by weight of N-(dichloroacetyl)diisobutylamine and the mixture of 2 parts by weight of amorphous silicic acid, 2 parts by weight of kieselguhr and 1 part by weight of powdered sulfite waste-liquor are ground in a laboratory Ultraplex beater-disc mill. The grist is homogenized together with 90 parts by weight of kieselguhr in a powder mixing equipment. The obtained powder product containing 5 percent by weight of an active agent has a wet sieve residue (on a 100μ sieve): maximum 2%.

EXAMPLE 5

5 parts by weight of N-dichloroacetyl-hexamethylenimine and 70 parts by weight of vaseline oil are homogenized in a laboratory mixer. Under stirring 5 parts by weight of nonyl phenol polyglycolether emulsifier are dissolved in 20 parts by weight of water. The mixture of the active agent and vaseline oil is added dropwise under intensive stirring into the aqueous solution of the tenside and the stirring is followed for 10 minutes.

An emulsion concentrate is obtained which contains 5 percent by weight of active agent and is dilutable with water.

EXAMPLE 6

80 parts by weight of N-(dichloroacetyl)-cyclohexyl-amine, 10 parts by weight of amorphous silicic acid, 2 parts by weight of alkyl-sulfonic acid-sodium wetting agent, 3 parts by weight of cresol-formaldehyde-condensate dispersing agent and 5 parts by weight of powdered sulfite waste-liquor are homogenized in a laboratory ball mill and preground, respectively, by one hour of grinding. The pregrist is fine ground under uniform addition in a laboratory beater-disc mill of type Ultraplex.

A wettable powder product is obtained which contains 80 percent by weight of active agent.
Floatability (in 1 percent concentration): 86.4%
Wet sieve residue (on a 50µ sieve): 3.8%

EXAMPLE 7

10 parts by weight of N-(dichloroacetyl)-benzylamine are dissolved in 30 parts by weight of dichloromethane under stirring, then 1 part by weight of polyoxyethylene-sorbitane-monolaurate wetting agent is added. The solution is sprayed onto 89 parts by weight of calcined kieselguhr granulate carrier through a shaking screen under shaking. The solvent is evaporated at a temperature of 50° C. in a drying cupboard and the granular material is dried until constant weight, it contains 10 percent by weight of active agent.
Corn size: between 0.2–1.0 mm.

EXAMPLE 8

50 parts by weight of N-(dichloroacetyl)-(6-ethyl-2-methyl)-aniline, 40 parts by weight of amorphous silicic acid, 3.5 parts by weight of cresol-formaldehyde precondensate, 1.5 parts by weight of aliphatic sulfonic acid-sodiumsalt and 5 parts by weight of powdered sulfite waste-liquor are mixed, then ground in a mill of type Alpine 100 LU and a 50 percent by weight wettable powder product (WP) is obtained.

EXAMPLE 9

One proceeds as in Example 8 and a 50 percent by weight wettable powder product is obtained from 50 parts by weight of N-(dichloroacetyl)-diisobutyl-amine.

EXAMPLE 10

One proceeds as in Example 8 and a 50 percent by weight wettable powder product is prepared from 50 parts by weight of N-(dichloroacetyl)-isopropyl-amine.

EXAMPLE 11

One proceeds as in Example 8 and a 50 percent by weight wettable powder product is prepared from 50 parts by weight of N-(dichloroacetyl)-cyclohexyl-amine.

EXAMPLE 12

One proceeds as in Example 8 and a 50 percent by weight wettable powder product is obtained from 50 parts by weight of N-(dichloroacetyl)-benzyl-amine.

EXAMPLE 13

One proceeds as in Example 8 and a 50 percent by weight wettable powder product is prepared from 50 parts by weight of N-(dichloroacetyl)-(4-methylbenzyl)-amine.

EXAMPLE 14

One proceeds as in Example 8 and a 50 percent by weight wettable powder product is prepared from 50 parts by weight of N-(dichloroacetyl)-3-chloroaniline.

EXAMPLE 15

One proceeds as in Example 8 and a 50 percent by weight wettable powder product is prepared from 50 parts by weight of N-(dichloroacetyl)-aniline.

EXAMPLE 16

Tests were carried out with an emulsion concentrate prepared according to Example 1 in order to influence the growth of plants belonging to the family of Graminea plants.

The tests were carried out in a glass-house, in a plastic forcing vessel with a surface of 120 cm$^2$, at first 400 g of soil were weighed into every vessel (the characteristics of the soil were as follows: humus contents: 2.2%, nitrogen contents: 0.1%, potassium oxide contents: 100 mg/100 g; phosphoruspentoxide contents: 60.0 mg/100 g; pH-value of the soil humidity: 7.4; its bondness: 37.6). Then 4 g each of the seeds of plants belonging to the Graminea family were put into the jar and covered with 100 g of soil each. Different quantities of the emulsion of the product according to Example 1 which was diluted with water were sprayed onto the surface of the soil, after this treatment further 200 g each of soil were weighed into the jars. The plants were cultivated—while ensuring a maximum water capacity of 65% by constant watering—under artificial daylight supplemental lamps with 14 hour lighting periods in a glass-house at a temperature of 18°–20° C.

The treatments were performed in twenty forcing jars each and repeated four times while plants were cultivated in untreated jars for comparison.

On the 14th day after the treatment the part of the plants above the soil was cut off, their green mass was weighed and it was compared with the green mass of the untreated plants.

The results of the tests are summarized in Table I.

TABLE I

| dose of treatment | | green mass of |
|---|---|---|
| number | active agent kg/ha | the plants in % |
| 1 | 0.16 | 143 |
| 2 | 0.32 | 196 |
| 3 | 0.65 | 225 |
| 4 | 1.30 | 271 |
| 5 | 2.60 | 321 |
| 6 | untreated | 100 |

The test results prove a very considerably stimulation of the growth. Already at a treatment of 0.16 kg/ha is the green mass of the treated plants by 43 percent bigger than that of the control plants, and at a dose of 0.32 kg/ha it is already the double while at a treatment of 2.60 kg/ha it exceeds the threefold.

EXAMPLE 17

The effect of the different doses of compounds of formula (I) on different test plants was examined.

The tests were performed in plastic jars with a surface of 113 cm² covered with a foil into which at first 400 g of soil per jar were filled (the characteristics of the soil: humus=1.39 percent by weight; nitrogen contents 3.10 mg/100 g; $pH_{H_2O}=8.2$), then the seeds of the test plants were put on it:

maize (Zea mays) MVTC-596 10 seeds/jar
millet (Panicum sp.) 30 seeds/jar
sorghum (Sorghum sp.) 20 seeds/jar.

The seeds were covered with 200 g of soil each and the chemical treatments were carried out in different doses by spraying onto the soil. The compositions of the invention were used in form of a 50 percent by weight WP (wettable powder). For comparison the same test plants were cultivated in untreated jars.

After the spraying the soil was watered until a water capacity of 65% and in the course of the cultivation the evaporated water was supplemented on the basis of weight measurement daily. The plants were cultivated under artificial daylight supplemental lamps with daylighting periods of 16 hours at a temperature of 18°–20° C.

The evaluation was performed on the 7th day after the treatment by weighing the green mass of the cut plants and the measurement results were related to the untreated control and their values were provided in percent.

The results of the tests are included in Tables II, III and IV.

TABLE II

Examination of the dose effect on the green weight of maize in percent

| No. | Compound of formula (I) | dose kg active agent/ha green weight in control % | | | | |
|---|---|---|---|---|---|---|
| | | 0.1 | 0.5 | 1.0 | 2.0 | 4.0 |
| 1. | Untreated control | 100 | 100 | 100 | 100 | 100 |
| 2. | N—(dichloroacetyl)-(6-ethyl-2-methyl)-aniline | 92.1 | 93.2 | 98.4 | 105.6 | 129.8 |
| 3. | N—(dichloroacetyl)-diisobutyl-amine | 108.8 | 109.5 | 106.1 | 110.6 | 118.0 |
| 4. | N—(dichloroacetyl)-isopropyl-amine | 90.8 | 117.2 | 123.8 | 121.7 | 119.3 |
| 5. | N—(dichloroacetyl)-cyclohexyl-amine | 106.2 | 106.8 | 94.9 | 103.0 | 93.7 |
| 6. | N—(dichloroacetyl)-benzyl-amine | 92.6 | 106.8 | 102.9 | 101.8 | 105.8 |
| 7. | N—(dichloroacetyl)-(4-methyl-benzyl)-amine | 104.2 | 94.9 | 110.7 | 89.3 | 71.7 |
| 8. | N—(dichloroacetyl)-3-chloroaniline | 120.2 | 155.2 | 104.1 | 100.8 | 110.8 |
| 9. | N—(dichloroacetyl)-aniline | 100.5 | 100.2 | 93.5 | 116.9 | 105.8 |
| 10. | N—(dichloroacetyl)-hexamethylene-imine | 112.3 | 116.8 | 118.5 | 120.3 | 125.7 |

TABLE III

Examination of the dose effect on the millet green weight in %

| No. | Compound of formula (I) | dose kg active agent/ha green weight in control % | | | | |
|---|---|---|---|---|---|---|
| | | 0.1 | 0.5 | 1.0 | 2.0 | 4.0 |
| 1. | Untreated control | 100 | 100 | 100 | 100 | 100 |
| 2. | N—(dichloroacetyl)-(6-ethyl-2-methyl)-aniline | 222.7 | 240.0 | 210.7 | 237.3 | 226.7 |
| 3. | N—(dichloroacetyl)-diisobutyl-amine | 225.3 | 217.3 | 197.3 | 260.0 | 229.3 |
| 4. | N—(dichloroacetyl)-isopropyl-amine | 233.3 | 186.7 | 197.3 | 233.3 | 230.7 |
| 5. | N—(dichloroacetyl)-cyclohexyl-amine | 224.0 | 260.0 | 249.3 | 201.3 | 197.3 |
| 6. | N—(dichloroacetyl)-benzyl-amine | 166.7 | 192.0 | 269.3 | 209.3 | 210.7 |
| 7. | N—(dichloroacetyl)-4-methyl-benzyl-amine | 217.3 | 216.0 | 190.7 | 197.3 | 229.3 |
| 8. | N—(dichloroacetyl)-3-chloro-aniline | 246.7 | 202.7 | 188.0 | 224.0 | 177.3 |
| 9. | N—(dichloroacetyl)-aniline | 209.3 | 250.7 | 250.7 | 257.3 | 249.3 |
| 10. | N—(dichloroacetyl)-hexamethylene-imine | 201.2 | 215.7 | 235.3 | 270.1 | 270.0 |

TABLE IV

Examination of the dose effect on the green weight of sorghum in %

| No. | Compound of formula (I) | dose kg active agent/ha green weight in control % | | | | |
|---|---|---|---|---|---|---|
| | | 0.1 | 0.5 | 1.0 | 2.0 | 4.0 |
| 1. | Untreated control | 100 | 100 | 100 | 100 | 100 |
| 2. | N—(dichloroacetyl)-(6-ethyl-2-methyl)-aniline | 113.5 | 117.1 | 116.2 | 107.2 | 104.5 |
| 3. | N—(dichloroacetyl)-diisobutyl-amine | 106.3 | 101.8 | 118.0 | 122.5 | 100.0 |
| 4. | N—(dichloroacetyl)-isopropyl-amine | 107.2 | 111.7 | 131.5 | 112.6 | 104.5 |
| 5. | N—(dichloroacetyl)-cyclohexyl-amine | 107.2 | 110.8 | 108.1 | 101.8 | 125.2 |
| 6. | N—(dichloroacetyl)-benzyl-amine | 107.2 | 112.6 | 120.7 | 108.1 | 118.0 |
| 7. | N—(dichloroacetyl)-4-methyl-benzyl-amine | 112.6 | 116.3 | 118.9 | 100.0 | 95.5 |
| 8. | N—(dichloroacetyl)-3-chloro-aniline | 103.6 | 119.8 | 112.6 | 109.9 | 107.2 |
| 9. | N—(dichloroacetyl)-aniline | 96.4 | 107.2 | 129.7 | 124.3 | 125.2 |
| 10. | N—(dichloroacetyl)-hexamethylene-imine | 102.5 | 106.3 | 112.4 | 118.6 | 119.0 |

Our examinations proved that several derivatives of the compounds of formula (I) cause a perceptible increase of the green mass at a treatment of already 0.1 kg of active agent/ha, while at treatments of 1–4 kg of active agent/ha the green mass of the plants is increased by 10 to 110 percent.

EXAMPLE 18

The effect of the compounds of the invention on the yield quantity was examined in open land small-plot experiments in a maize and a sugar beet culture. The tests were repeated four times at 20 plots each with a surface of 98 m². In the course of the treatments the 50 percent by weight composition EC diluted with water was sprayed twice, at the maize of first at the beginning of the tasseling, then at the full blooming, at the sugar beet, however, at first at the closening of the lines, then at the time of the protection against the last cercospore in a dose of 6 l/ha. 300 l of water were used per ha.

The effect of the composition was evaluated on the basis of the obtained yield quantities and compared with the yield quantities of the untreated controls.

The obtained results are included in Tables V and VI.

TABLE V

Development of the yield of crude corn maize

| No. | Treatment | yield t/ha | deviation from the control ± t/ha | % |
|---|---|---|---|---|
| 1 | Untreated control | 6.38 | — | 100 |
| 2 | N—(dichloroacetyl)-hexamethylene-imine | 7.21 | +0,83 | 113 |

TABLE VI

Development of the beet and sugar yield

| | beet yield | | | sugar yield | |
|---|---|---|---|---|---|
| No. | Treatments | t/ha | deviation from the control ± t/ha | measured sugar contents % | t/ha | deviation from the control ± t/ha |
| 1. | untreated control | 34.52 | — | 16.08 | 5.55 | — |
| 2. | N—(dichloroacetyl)-hexamethylene-imine | 44.55 | +10.03 | 17.00 | 7.57 | +2.0 |

The open land examinations, too, proved that the corn yield is increased significantly, to a degree exceeding 10 percent by weight in the case of maize.

In the case of sugar beet not only the quantity of the yield increased by more than a third but the sugar contents of the crude beet, too, rose and the sugar yield to be attained from an area of 1 ha improved and was 36 percent higher than at the untreated plot.

We claim:

1. A method of stimulating the growth and green weight of millet or sorghum plants growing upon a plant site, comprising applying to said site 0.1 to 4.0 kg/ha of a compound of formula (I)

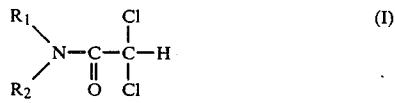

wherein $R_1$ and $R_2$ are identical or different and each is hydrogen, a $C_{1-4}$ straight or branched alkyl group, cyclohexyl, phenyl, chlorophenyl, $C_1$–$C_4$ alkylphenyl, benzyl or $C_1$–$C_4$ alkylbenzyl group, or $R_1$ and $R_2$ together with the N atom form a hexamethyleneimino ring in a composition containing said compound together with a solid or liquid carrier and at least one surface-active agent.

2. The method defined in claim 1 which contains 5 to 80% by weight of said compound, 10 to 95% by weight of a solid carrier in the form of a synthetic amorphous silicic acid or a mineral of silicate type as well as 0.5 to 15% by weight of at least one surface-active agent.

3. The method defined in claim 1 which contains 5 to 80% by weight of said compound, 10 to 95% by weight of a water-immiscible solvent in the form of a halogenated or aromatic hydrocarbon as well as 0.5 to 15% by weight of at least one surface-active agent.

4. The method defined in claim 1 which contains 5 to 80% by weight of said compound, 10 to 95% by weight of a solid carrier in the form of a synthetic amorphous silicic acid or a mineral of silicate type and/or a liquid carrier in the form of a synthetic mineral white-oil fraction or a water-immiscible organic solvent in the form of a halogenated or aromatic hydrocarbon as well as 0.5 to 15% by weight of at least one surface-active agent.

5. A method as defined in claim 2 wherein said surface-active agent includes at least one melting and dispersing agent.

6. A method as defined in claim 3 wherein said surface-active agent includes a mixture of anionic and non-ionic tensides.

7. A method as defined in claim 4 wherein said surface-active agent includes a mixture of anionic and non-ionic tensides.

8. The method of stimulating the growth and green weight of plants growing upon a plant site, defined in claim 8, wherein in the compound of the formula I, $R_1$ and $R_2$ are identical or different, and each is hydrogen, a $C_1$–$C_4$ straight or branched chain alkyl group, cyclohexyl, phenyl, chlorophenyl, $C_1$–$C_4$ alkylphenyl, benzyl, or $C_1$–$C_4$ alkyl-benzyl.

9. The method defined in claim 8 wherein the compound of the formula I is N-dichloroacetyl-cyclohexylamine.

10. A method of stimulating the growth and green weight of a maize plant growing on a plant site, comprising applying to said site 0.1 to 0.5 kg/ha of a compound selected from the group consisting of:
    (a) N-(dichloroacetyl)-cyclohexylamine;
    (b) N-(dichloroacetyl)-diisobutylamine;
    (c) N-(dichloroacetyl)-3-chloroaniline;
    (d) N-(dichloroacetyl)-aniline; and
    (e) N-(dichloroacetyl)-hexamethyleneimine, in a composition containing said compound together with a solid or liquid carrier and at least one surface-active agent.

11. A method of stimulating the growth and green weight of a maize plant growing on a plant site, comprising applying to said site 2.0 kg/ha of a compound selected from the group consisting of:
    (a) N-(dichloroacetyl)-cyclohexylamine;
    (b) N-(dichloroacetyl)-(6-ethyl-2-methyl)-aniline;
    (c) N-(dichloroacetyl)-diisobutylamine;
    (d) N-(dichloroacetyl)-isopropylamine;
    (e) N-(dichloroacetyl)-benzylamine;
    (f) N-(dichloroacetyl)-(4-methylbenzyl)-amine;
    (g) N-(dichloroacetyl)-3-chloroaniline; and
    (h) N-(dichloroacetyl)-hexamethyleneimine, in a composition containing said compound together with a solid or liquid carrier and at least one surface-active agent.

* * * * *